US011779546B2

(12) United States Patent
Petyaev

(10) Patent No.: US 11,779,546 B2
(45) Date of Patent: Oct. 10, 2023

(54) DISASSEMBLY OF CHOLESTEROL CRYSTALS

(71) Applicant: IP SCIENCE LIMITED, Cambridge (GB)

(72) Inventor: Ivan Petyaev, Cambridge (GB)

(73) Assignee: IP SCIENCE LIMITED, Cambridge (GB)

( * ) Notice: Subject to any disclaimer, the term of this patent is extended or adjusted under 35 U.S.C. 154(b) by 411 days.

(21) Appl. No.: 16/967,854

(22) PCT Filed: Feb. 7, 2019

(86) PCT No.: PCT/GB2019/050335
§ 371 (c)(1),
(2) Date: Aug. 6, 2020

(87) PCT Pub. No.: WO2019/155217
PCT Pub. Date: Aug. 15, 2019

(65) Prior Publication Data
US 2021/0030696 A1    Feb. 4, 2021

(30) Foreign Application Priority Data
Feb. 7, 2018 (GB) .................................. 1801987

(51) Int. Cl.
*A61K 31/01* (2006.01)
*A61P 3/06* (2006.01)
*A61K 9/00* (2006.01)

(52) U.S. Cl.
CPC ............ *A61K 31/01* (2013.01); *A61K 9/0024* (2013.01); *A61P 3/06* (2018.01)

(58) Field of Classification Search
CPC ... A61K 31/01; A61P 3/06; A61P 9/10; A61L 2300/422; C07B 2200/13
See application file for complete search history.

(56) References Cited

FOREIGN PATENT DOCUMENTS

CN         101264345       *  9/2008
CN         101264345 A     *  9/2008

OTHER PUBLICATIONS

Mozos et al, Lycopenes and Vascular Health, rom. Pharmacol., Sec. Ethnopharmacology, vol. 9 (Year: 2018).*
Patyeav, Lycopene Reduces Formation of Cholesterol Crystals and Accelerates Their Dissolution, Circulation, vol. 144, Issue Sppl_1 . . . (Year: 2021).*
Rajendran, et al., "Subcellular targeting strategies for drug design and delivery", Nature Reviews Drug Discovery, 2010, vol. 9, pp. 29-42.
Hawkes et al., "Lipid Membrane; a Novel Target for Viral and Bacterial Pathogens", Current Drug Targets, 2006, vol. 7, No. 12, pp. 1615-1621.
Dowing, RH, "Review: pathogenesis of gallstones", Aliment Pharmacol Ther., 2000, vol. 14, Suppl 2, pp. 39-47.
Strasberg et al., "Pathogenesis of Cholesterol Gallstones—A Review", HPB Surgery, 1991, vol. 3, pp. 79-102.

(Continued)

*Primary Examiner* — Carlos A Azpuru
(74) *Attorney, Agent, or Firm* — Wenderoth, Lind & Ponack, L.L.P.

(57) ABSTRACT

The invention relates to methods for disrupting cholesterol crystals and related methods for the prevention and/or treatment of disease.

7 Claims, 9 Drawing Sheets

(56) References Cited

OTHER PUBLICATIONS

Figure 1:
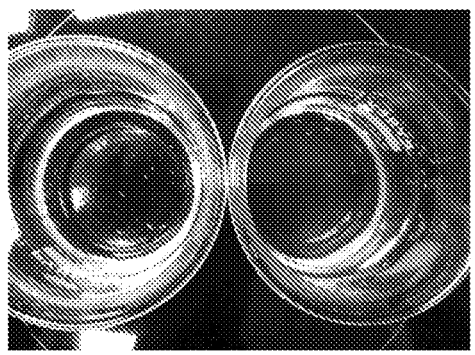
Figure 1:
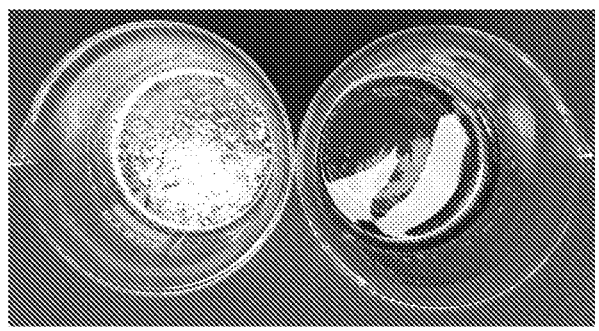
Figure 1:
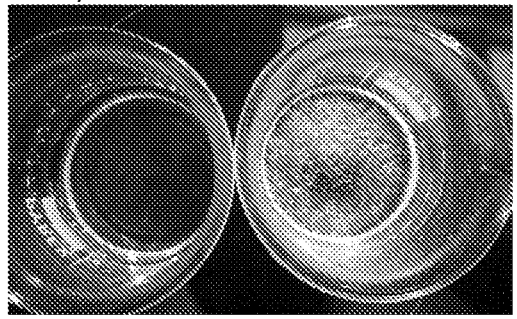
Figure 1:
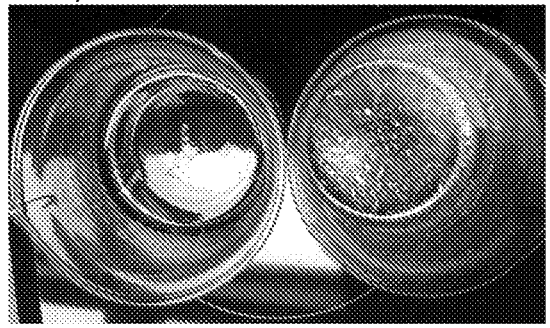
Figure 1:
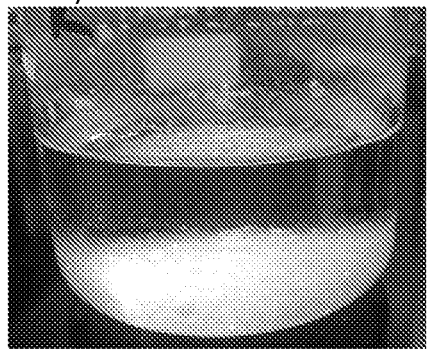
Figure 1:
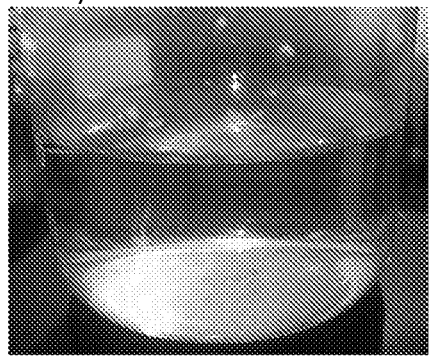
Figure 1:
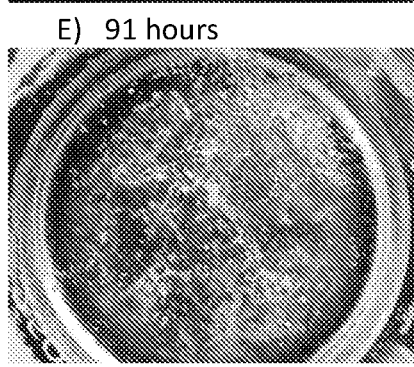
Figure 1:
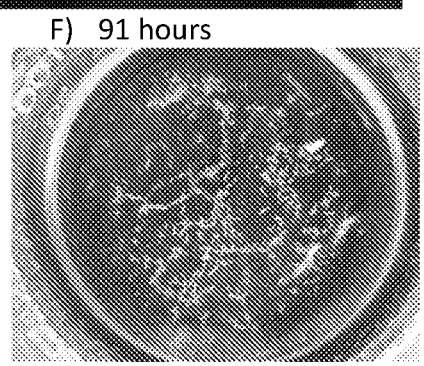
Figure 1:
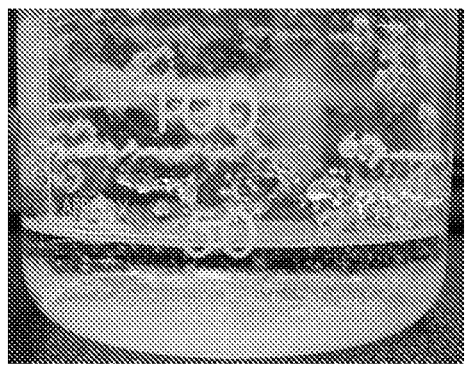
Figure 1:
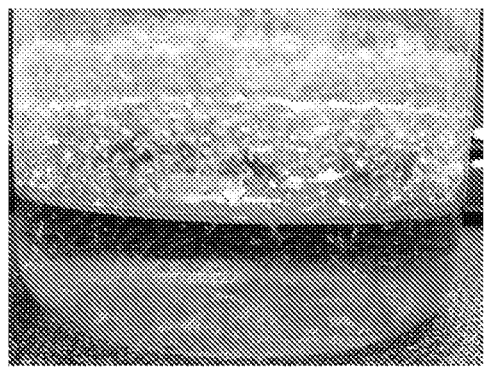
Figure 1:
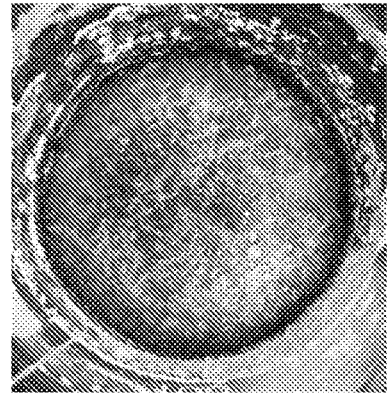
Figure 1:
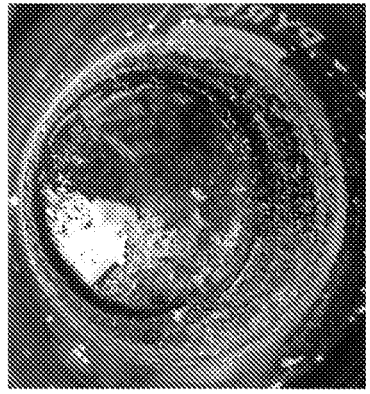
Figure 1:
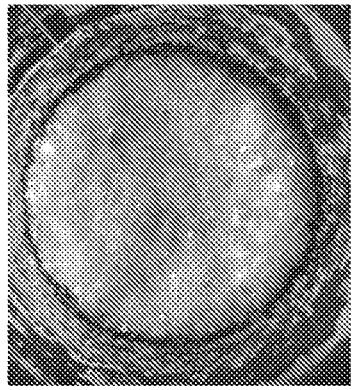
Figure 1:
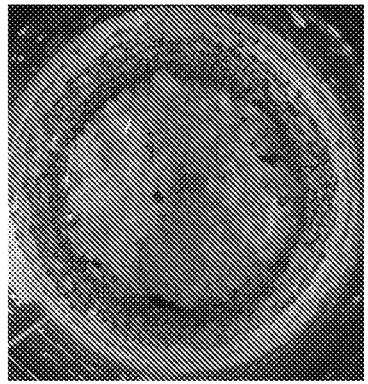

Stinton et al., "Epidemiology of Gallbladder Disease: Cholelithiasis and Cancer", Gut and Liver, 2012, vol. 6, No. 2, pp. 172-187.
Abela et al., "Cholesterol Crystals Rupture Biological Membranes and Human Plaques during Acute Cardiovascular Events—A Novel Insight into Plaque Rupture by Scanning Electron Microscopy", Scanning, 2006, vol. 28, pp. 1-10.
Abela, George S., "Cholesterol crystals piercing the arterial plaque and intima trigger local and systemic inflammation", Journal of Clinical Lipidology, 2010, vol. 4, pp. 156-164.
Frank, Richard J., "Parallel cholesterol crystals: A sign of impending plaque rupture", J Clin Exp Cardiolog, 2013, vol. 4, p. 74.
Conti, Richard, "Hypothermia: Is it Good for the Brain and Not for the Arteries?", JACC, 2013, vol. 61, No. 20, pp. 2110-2114.
Yamaji et al., "Bare metal stent thrombosis and in-stent neoatherosclerosis", Cir Cardiovasc Interv., 2012, vol. 5, No. 1, pp. 47-54.
Kang et al., "Multimodality imaging of attenuated plaque using grayscale and virtual histology instravascular ultrasound and optical coherent tomography", Catheter Cardiovasc Interv, 2016, vol. 88, No. 1, E1-E11.
Takigawa et al., "Recurrent subacute in-stent restenosis after carotid artery stenting due to plaque protrusion", Neurol Med Chir, 2009, vol. 49, No. 9, pp. 417-417.
Rodriguez et al., "Multiple microcrystal deposition disease in a patient with systemic lupus erythematosus", Ann Rheum Dis, 1984, vol. 43, pp. 498-502.
Hurley et al., "Identifying anterior segment crystals", 1991, British Journal of Ophthalmology, vol. 75, pp. 329-331.
Iqbal, Firoz, "The relationship between cholesterol crystals, foamy macrophages and haemosiderin in odontogenic cysts", 2008, Master of Dental Science, The University of Sydney, New South Wales, Australia, pp. 1-96.
Bessa da Motta Almada et al., "Cholesterol Granuloma of the Maxillary Sinus", 2008, Braz Dent J, vol. 19, No. 2, pp. 171-174.
Gowreeson et al., "Cholesterol granuloma of the kidney mimicking a tumour", 2003, Nephrol Dial Transplant, vol. 18, pp. 2449-2450.
Parkes Weber et al., "Cholesterol Tumour (Craniopharyngioma) of the Pituitary Body", 1934, J Neurol Psychopathol, S1-15, pp. 39-45.
Richter et al., "Anisotropic Crystals in the Human Thyroid Gland", 1954, Am J Pathol, vol. 30, No. 3, pp. 545-553.
Channabasaveshwar et al., "Cholesterol-based nonsymmetric liquid crystal dimers: an overview", 2008, J Mater Chem., vol. 18, pp. 2927-2949.
Abhijit, R., "Liquid Crystal—A Review", Asian Journal of Research in Chemistry, 2012, vol. 5, No. 4, pp. 563-567.
Jong et al., "Creation of Double Silica Nanotubes by Using Crown-Appended Cholesterol Nanotubes", 2003, Chemistry a European Journal, vol. 9, No. 21, pp. 5307-5313.
Xing et al., "Photo-triggered transformation from vesicles to branched nanotubes fabricated by a cholesterol-appended cyanostilbene", 2015, Chem. Commun., vol. 51, pp. 9309-9312.
Abela, George S., "Role of cholesterol crystals in myocardial infarction and stroke", 2010, Clinical Lipidology, vol. 5, No. 1, pp. 57-69.
Ridker, P.M.., "The Jupiter Trial—Results, Controversies, and Implications for Prevention", 2009, Circ Cardiovasc Qual Outcomes, vol. 2, pp. 279-285.
Nidorf et al., "Targeting Cholesterol Crystal-Induced Inflammation for the Secondary Prevention of Cardiovascular Disease", 2013, Journal of Cardiovascular Pharmacology and Therapeutics, vol. 19, No. 1, pp. 1-8.
Johnson et al., "Traditional Clinical Risk Assessment Tools Do Not Accurately Predict Coronary Atherosclerotic Plaque Burden: A CT Angiography Study", 2009, American Journal of Roentgenology, vol. 192, pp. 235-243.
Petersen et al., "Plasma lipid oxidation predicts atherosclerotic status better than cholesterol in diabetic apolipoprotein E deficient mice", 2017, Experimental Biology and Medicine, vol. 242, pp. 88-91.
Eder et al., "Reactive Oxygen Metabolites Promote Cholesterol Crystal Formation in Model Bile: Role of Lipid Peroxidation", 1996, Free Radical Biology & Medicine, vol. 20, No. 5, pp. 743-749.
Worthington et al., "Dietary Antioxidant Lack, impaired hepatic glutathione reserve, and cholesterol gallstones", 2004, Clinica Chimica acta, vol. 349, No. 1-2, pp. 157-165.
Buschman et al., "Raman Microspectroscopy of Human Coronary Atherosclerosis: Biomedical Assessment of Cellular and Extracellular Morphologic Structures in situ", 2001, Cardiovascular Pathology, vol. 10, No. 2, pp. 69-82.
International Search Report dated Apr. 15, 2019 in International (PCT) Application No. PCT/GB2019/050335.
Abela et al., "Effect of Cholesterol Crystals on Plaques and Intima in Arteries of Patients With Acute Coronary and Cerebrovascular Syndromes", 2009, American J. Cardiology, 103:959-968.
Lorenz et al., "Effects of Lycopene on the Initial State of Atherosclerosis in New Zealand White (NZW) Rabbits", 2012, PLOS One, vol. 7, No. 1 p. e30808.

\* cited by examiner

A) 18 hours

B) 56 hours

C) 67 hours

D) 80 hours

E) 91 hours

F) 91 hours

G) 138 hours

H) 138 hours

I) 204 hours

J) 204 Hours

K) 278 hours

L) 278 Hours

M) 332 hours

N) 332 Hours

A)

B)

Growing crystals – Experiment 1, lycopene to cholesterol ratio is 1 : 100,000

C)

D)

Growing crystals – Experiment 2, lycopene to cholesterol ratio is 1 : 1,000,000

E) Cholesterol

F) Lycopene-Cholesterol

G) Lycopene oleoresin

Experiment – 3

Dried crystals – experiment b

A) Growing LC

B) Needle / Tube LC

A)          B)          C)          D)

E) CC

F) LC

20µm 2,576 × 1,936

A) CC
B) LC

A)

Lycopene: Cholesterol

Control | 1:1,000,000 | 1:100,000 | 1:10,000 | 1:1,000

B) C) D) E) F)

A)

B) Cholesterol control crystals

C) Lutein : Cholesterol 1 : 50,000

A) Control  B) Phosphatidylcholine  C) Olive oil

D) Ground nut oil  E) Grape seed oil  F) Rapeseed oil

G) Coconut oil  H) Avocado oil  I) Hazelnut oil

J) Control  K) Almond oil  L) Sunflower oil  M) Tocopherol

PBS - Ethanol

A) 0 day

B) 13 days

PBS – Lycopene in Ethanol

C) 0 day

D) 13 days

PBS – Lycopene in Ethanol

E) 0 day

F) 13 days

DISASSEMBLY OF CHOLESTEROL CRYSTALS

INTRODUCTION

Cholesterol is an essential lipid in vertebrates that is derived from nutrition and from endogenous biosynthesis. As an ubiquitous component of all cellular membranes, it plays an essential role in membrane structure and function and it is important for maintaining membrane permeability and cell signalling. Free cholesterol has very low solubility in aqueous environments and lipoproteins serve as cholesterol carriers for cholesterol transport in the bloodstream.

However, cholesterol is also found in the body in its crystalline form. For example, solid cholesterol monohydrate crystals can be found in atherosclerotic plaque. Plaque cholesterol in the crystalline state is relatively inert, and may be extremely difficult or even impossible to immobilize, to disassemble and/or dissolve in an in vivo situation.

There are a number of medical areas, with two main fields, where clusterisation or crystallisation of cholesterol, its metabolites and derivatives have significant importance.

The first field covers such important applications from targeting cholesterol-rich lipid rafts, as dynamic microdomains in plasma membrane to gallstones formed in the gallbladder and cholesterol crystals growing in arterial atherosclerotic plaques. Control of the cholesterol clusterisation would affect the dynamics of the lipid rafts which could be important in regulation of a number of membrane functions from receptor expression and signalling to transport of ions, nutrients, regulating molecules and pathogens [1, 2]

The other medical area where control of formation of cholesterol crystals or aggregates is important is the gallstone pathology [3, 4]. Gallstone disease is a common and costly serious medical condition, which affect 10 to 15% of adult population in the developed world. For example more than 20-25 million Americans suffer from this disease, and it costs $6.2 billion annually in the US, constituting one of the main health burden.

However, the main health problem is formation of cholesterol crystals in arterial atherosclerotic plaques. Their growth and eventual protrusion into the vascular lumen is considered as one of the leading courses of the rapture of the vulnerable plaque and clotting which can lead to a heart attack or myocardial infarction, a stroke and other complications of the acute thrombosis [6-10].

Cholesterol crystals have thus long been identified within atherosclerotic plaque, and their potential to play a causative role in atherosclerosis was first recognized more than 50 years ago when experiments in animals demonstrated that when injected into the arterial wall they led to the development of typical atherosclerotic lesions. Cholesterol within atherosclerotic plaque is mostly esterified; however, as plaques develop, the amount of free cholesterol within them increases and predisposes to the formation of techniques have demonstrated the presence of cholesterol crystals in nascent plaques cholesterol crystals. Recent advances in imaging and staining and much higher concentrations of cholesterol crystals in vulnerable and unstable atherosclerotic plaque [27]. Cholesterol crystallization and associated volume expansion with sharply tipped crystals can disrupt the fibrous cap and lead to plaque rupture [25].

Cardiovascular disease remains the leading cause of mortality in the developed world and 19 million people died from it in 2014 with the global cost of more than $900 billion. Only in the US more than 6 million people over 20 years of age have had a stroke. Every year about 1 million there experience a new or recurrent stroke. Atherosclerosis is responsible for the vast majority of cardiovascular diseases. Despite decades of work, statins and PCSK9 inhibitors, the drugs which reduce blood cholesterol level, remain the only effective therapy, but they can only slow, not stop or reverse disease progression. There is no currently available therapy to stop the development of atherosclerosis and induce its regression.

It is known that total blood cholesterol has poor correlation with development of the atherosclerotic plaque [29]. It is also known that total serum cholesterol does not correlate with atherosclerotic plaque burden [28]. Furthermore, 50% patients with heart attack do not have elevated blood cholesterol [26]. New strategies for the treatment of cardiovascular disease in the absence of hyperlipidimia are therefore required. Cholesterol crystals are an independent risk factor for the development of cardiovascular disease, that is independent of high serum (circulating) cholesterol level. Moreover, plaque rupture and release of cholesterol in its crystalline form can trigger the acute clinical events myocardial infarction and stroke.

Another medical problem where cholesterol growth and atherogenesis cause a serious complication is a reconstructive intravascular treatment with stents and other intravascular devices. These non-surgical procedures are quick with minimal traumatic experience to patients, less complicated and with relatively low cost have become a common practice replacing open-heart cardiovascular and other by-pass surgeries.

However, the main complication of using stents and other similar treatments is a very high rate of re-stenosis. This is caused by so-called "neoathersoclerosis" where atheromatous mass starts to grow and a build up of cholesterol crystals take place [11-13].

There are other medical conditions associated or caused by crystallisation or aggregation of cholesterol or its derivatives or metabolites. They are: a build up of cholesterol crystals in synovial liquid in Lupus Erythematosus [14], in the anterior segment of the eye in patients with hypermature cataract [15], in odontogenic cysts [16], cholesterol granulomas growth was observed in chronic disease of the middle ear and paranasal synuses [17], in the kidney [18], in the pituitary [19] and thyroid glands [20].

There is therefore a need to treat and prevent formation and growth of cholesterol crystals, in particular as new methods for the treatment, prevention or amelioration of atherosclerosis are needed in the art.

SUMMARY

The inventor has found that carotenoid compounds have an effect on the formation, growth and stability of cholesterol crystals as well as on their structure and/or size. This finding can be applied to treat a number of diseases that are associated with the presence of cholesterol crystals in a subject.

In one aspect, there is provided a carotenoid compound for use in the treatment of a disease associated with the presence of cholesterol crystals in a subject wherein the carotenoid compound reduces one or more of the formation, size or growth of cholesterol crystals, and/or changes cholesterol crystal structure. For example, the carotenoid compound reduces the rate of formation and/or the rate of growth of cholesterol crystals.

In one embodiment, the carotenoid compound reduces the rate of crystallisation.

In one embodiment, the carotenoid compound changes cholesterol structure.

In one embodiment, the carotenoid compound disrupts cholesterol crystals.

In one embodiment, the carotenoid compound delays the formation of cholesterol crystals In one embodiment, the carotenoid compound facilitates disassembly and/or dissolution of cholesterol crystals.

In one embodiment, the carotenoid compound is selected from lycopene, lutein, zeaxanthin, meso-zeaxanthin, astaxanthin, carotenes, cryptoxanthins, flavoxanthin, neoxanthin or another tetraterpenoid.

In one embodiment, the carotenoid compound is a lycopene.

In one embodiment, the disease is selected from a cardiovascular disease, cerebrovascular disease, peripheral artery disease, aortic or arterial aneurysm, cholelithiasis and gallstone disease, renal artery stenosis, eye stroke, erective dysfunction, mesenteric or intestinal ischemia, Lupus Erythematosus, hypermature cataract, odontogenic cysts, chronic disease of the middle ear and paranasal synuses, renal disease or thyroid disease.

In one embodiment, the carotenoid compound is administered as part of a food stuff.

In one embodiment, the food stuff is a dietary supplement, nutracosmetic or nutraceutical product.

In one aspect, we provide a method for the prevention or treatment of a disease associated with the presence of cholesterol crystals in a subject comprising administering to said subject a carotenoid compound wherein said carotenoid compound reduces the growth, size and/or formation of cholesterol crystals, and/or disrupts, facilitates disassembly or dissolution of cholesterol crystals.

In one embodiment, the carotenoid compound reduces the growth and/or formation of cholesterol crystals. For example, the carotenoid compound reduces the rate of formation and/or rate of growth of cholesterol crystals.

In one embodiment, the carotenoid compound disrupts or facilitates disassembly or dissolution of cholesterol crystals.

In one embodiment, the carotenoid compound is selected from a lycopene, lutein, zeaxanthin, meso-zeaxanthin, astaxanthin, carotenes, cryptoxanthins, flavoxanthin, neoxanthin or another tetraterpenoids. In one embodiment, the compound is a lycopene.

In one embodiment, the disease is selected from cardiovascular disease, Lupus Erythematosus, hypermature cataract, odontogenic cysts, chronic disease of the middle ear and paranasal synuses, renal disease or thyroid disease.

In one embodiment, the carotenoid compound is administered as part of a food stuff.

In one embodiment, the food stuff is a dietary supplement, nutracosmetic or nutraceutical product.

In another aspect, the invention provides the use of a carotenoid compound in the manufacture of a stent or other graft, medical device, prosthetic or other biocompatible material for the prevention or treatment a disease associated with cholesterol crystals wherein said carotenoid compound reduces the formation of cholesterol crystals or disrupts cholesterol crystals.

In yet another aspect, the invention provides a stent or other graft, medical device, prosthetic or other biocompatible material coated with a carotenoid compound.

The invention also provides a method for making a stent or other graft, medical device, prosthetic or other biocompatible material comprising the step of coating the stent or other graft, medical device, prosthetic or other biocompatible material with a carotenoid compound.

We also provide an in vitro or in vivo method for changing cholesterol crystal structure, reducing formation, growth or size of cholesterol crystals comprising exposing a cholesterol crystal to a carotenoid compound.

We further provide a cholesterol crystal obtained or obtainable by the method above.

FIGURES

The invention is further illustrated in the following non-limiting figures.

FIG. 1. Lycopene prevents or slows down formation of cholesterol crystallisation. A) 18 hours; B) 56 hours; C) 67 hours; D) 80 hours; E) and F) 91 hours; G) and H) 138 hours; I) and J) 204 hours; K) and L) 278 hours; M) and N) 332 hours.

Figure 2:
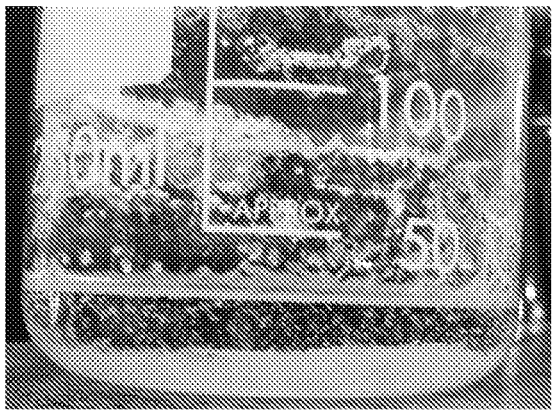
Figure 2:
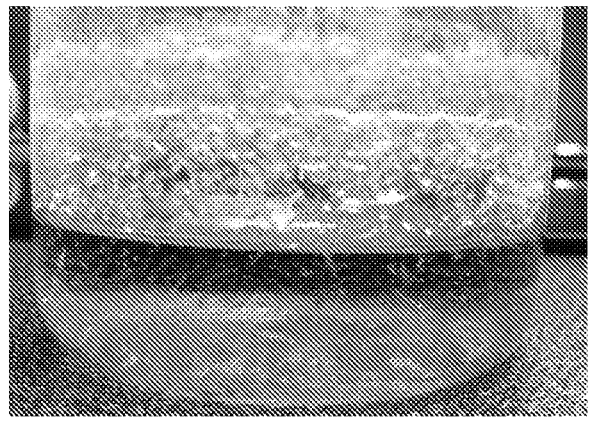
Figure 2:
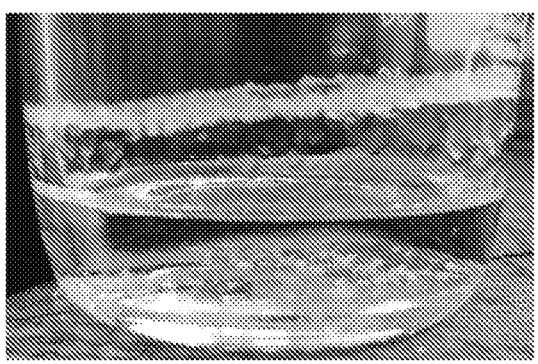
Figure 2:
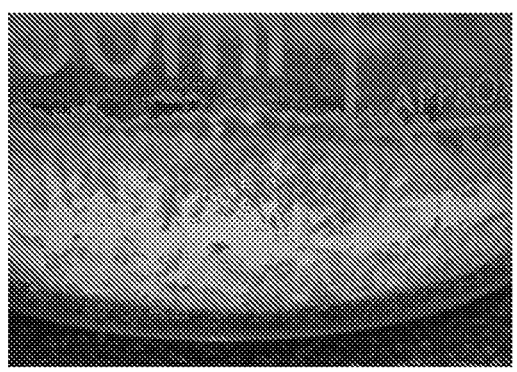
Figure 2:
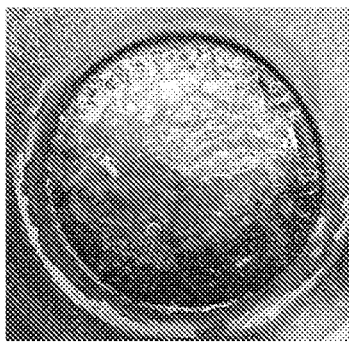
Figure 2:
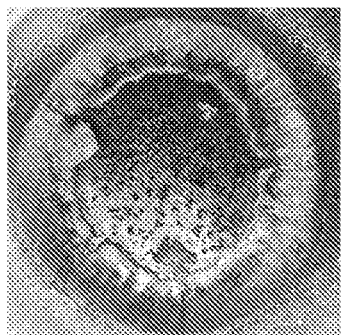
Figure 2:
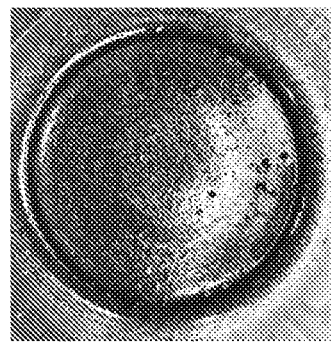

FIG. 2. Formation of plate-like cholesterol crystals (on the left) in the control solutions and needle-like crystals under the influence of lycopene (on the right). A) and B) experiment 1, lycopene to cholesterol ratio is 1:100,000; C) and D) experiment 2, lycopene to cholesterol ratio is 1:1,000,000; E)-F) experiment 3 (E-Cholesterol, F-Lycopene-Cholesterol, G-Lycopene oleoresin).

Figure 3:
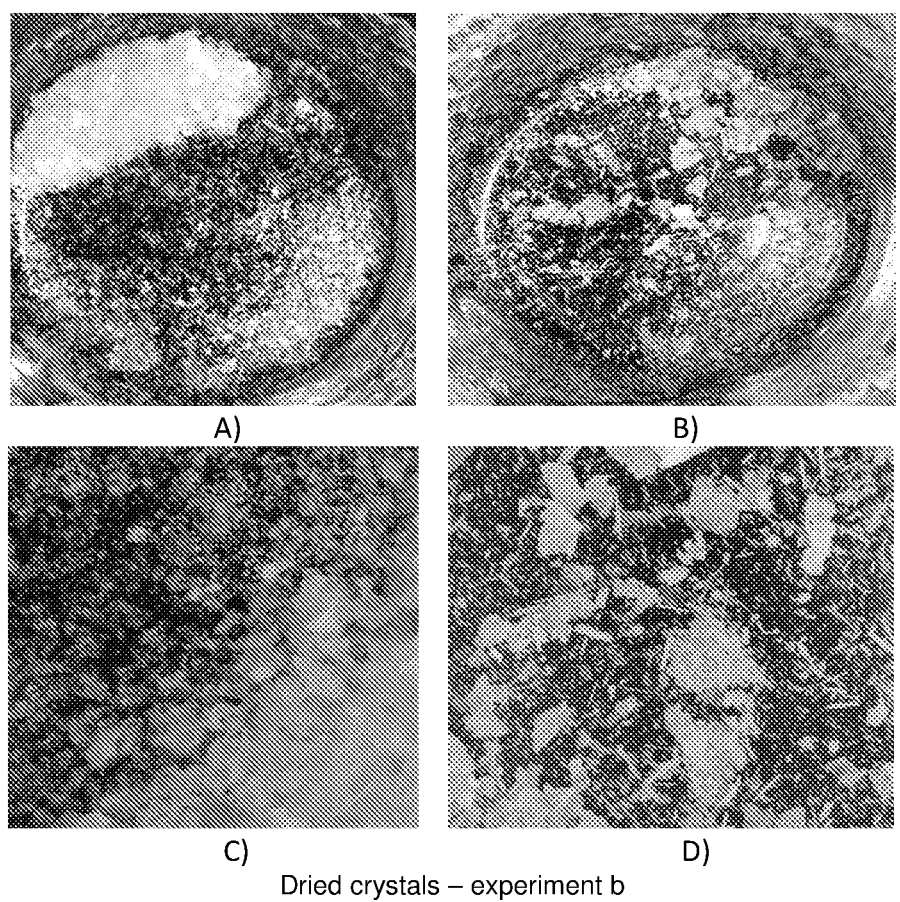

FIG. 3. A-D) Different type of cholesterol crystals formed with (right) and without lycopene (left). Dried crystals, experiment b.

Figure 4:
Figure 4:
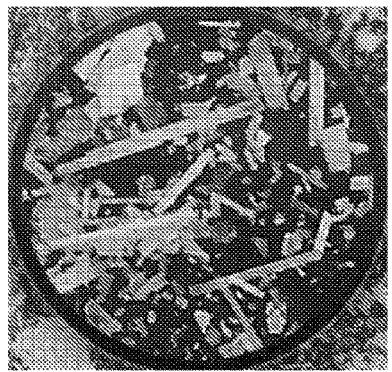

FIG. 4. Formation of needle type cholesterol crystals under the influence of lycopene (LC), lycopene to cholesterol ratio was 1:1,000,000. A) growing LC; B) needle/tube LC.

Figure 5:
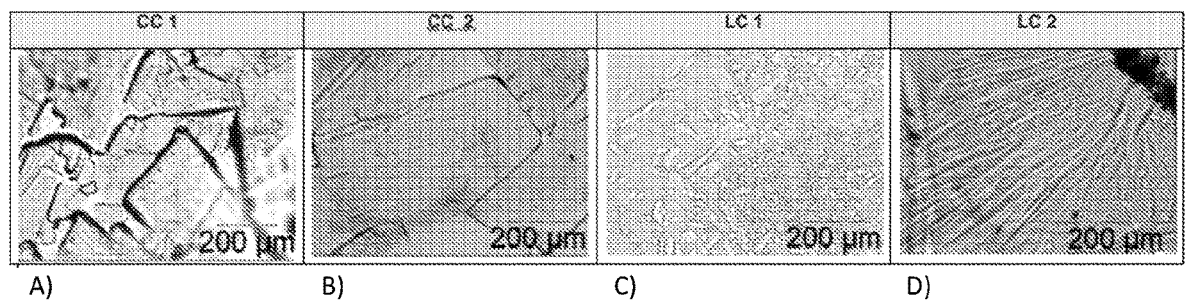
Figure 5:
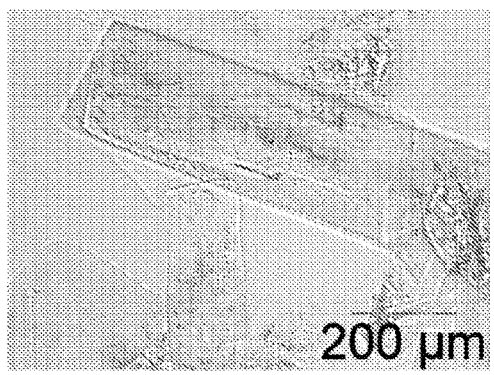
Figure 5:
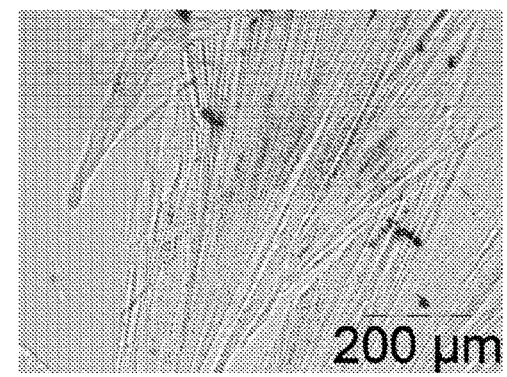

FIG. 5. Light microscopy of the control cholesterol crystals, CC, and formed with presence of lycopene, LC. A) CC1; B) CC2; C) LC1; D) LC2; E) CC; F) LC.

Figure 6:
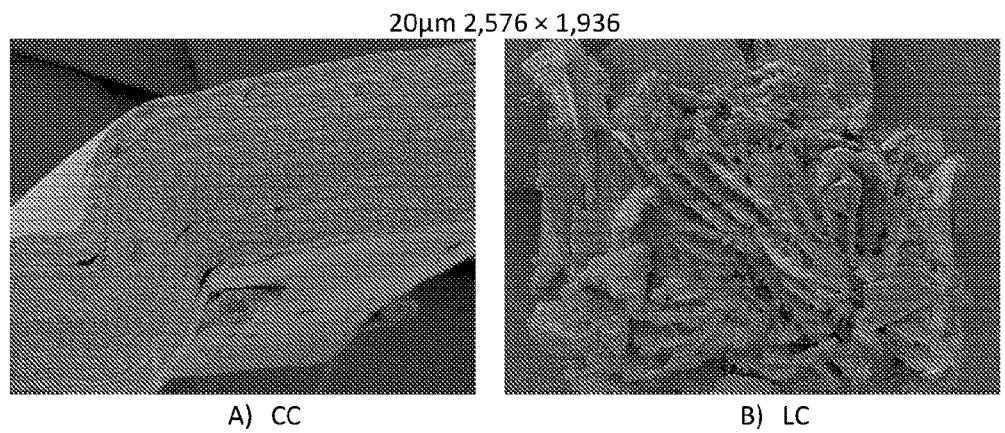

FIG. 6. A) Confocal microscopy of the control cholesterol crystals, CC, and B) formed with presence of lycopene, LC.

Figure 7:
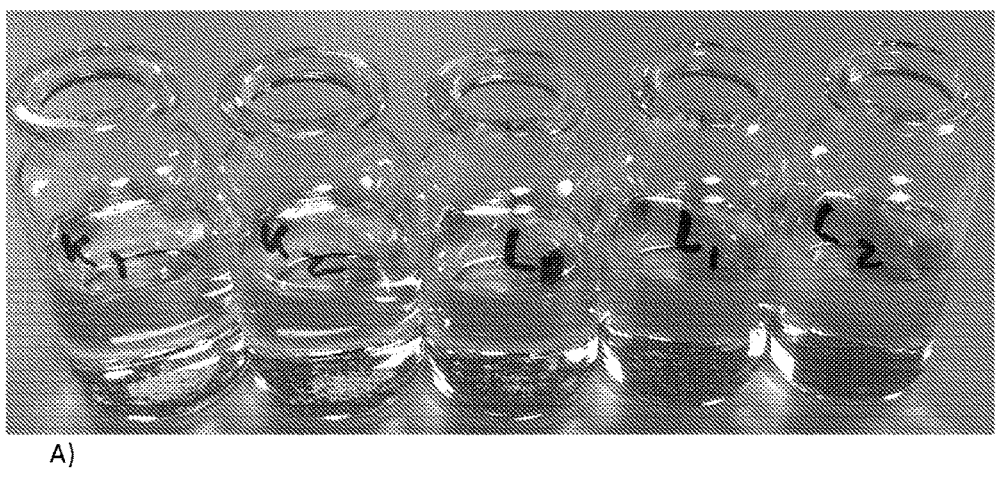
Figure 7:
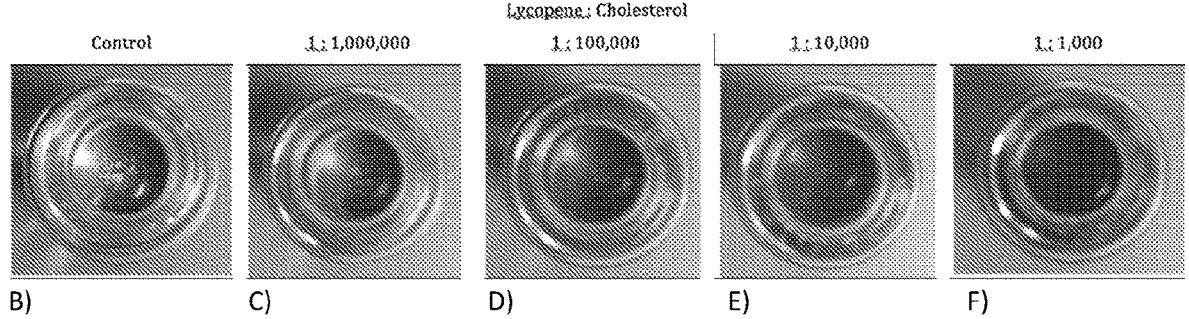

FIG. 7. A) Dissolution of Cholesterol Crystals by different concentrations of lycopene, experiment 1. K1 and K2-control samples, L0-0.01 µg/ml, L1-0.05 µg/ml, L2-0.1 µg/ml. B-F) Dissolution of Cholesterol Crystals by different concentrations of lycopene, experiment 2. B) control; C) lycopene-cholesterol ratio 1:1,000,000; D) lycopene-cholesterol ratio 1:100,000; E) lycopene-cholesterol ratio 1:10,000; F) lycopene-cholesterol ratio 1:1,000.

Figure 8:
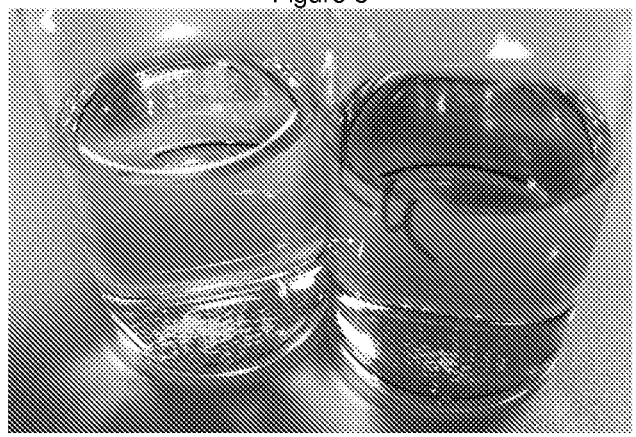
Figure 8:
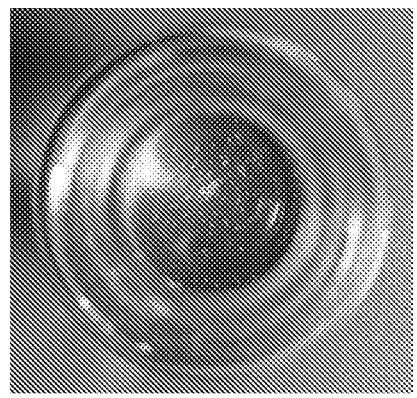
Figure 8:
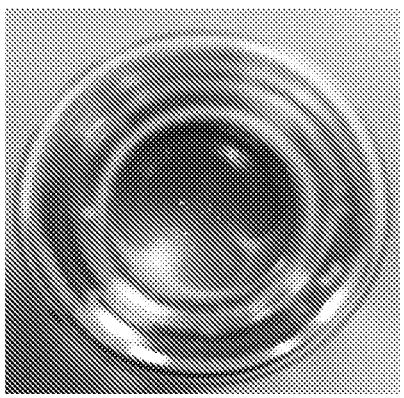

FIG. 8. A) Dissolution of Cholesterol Crystals by lutein, experiment 1. Left—control cholesterol crystals, right—lutein to cholesterol 1:100,000. B-C) Dissolution of Cholesterol Crystals by lutein, experiment 2, B) cholesterol control crystals; C) Lutein: Cholesterol ration 1:50,000.

Figure 9:
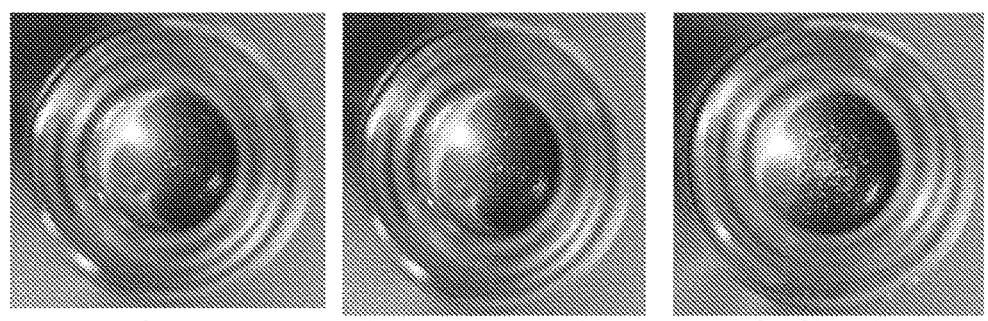
Figure 9:
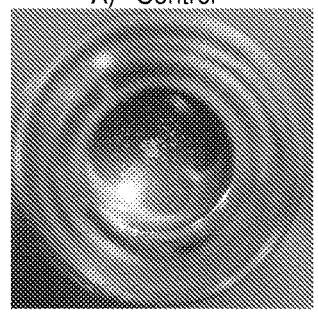
Figure 9:
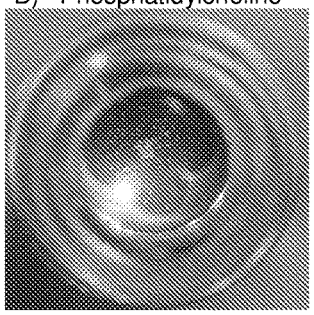
Figure 9:
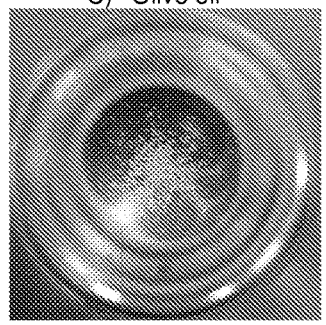
Figure 9:
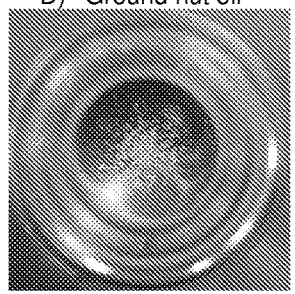
Figure 9:
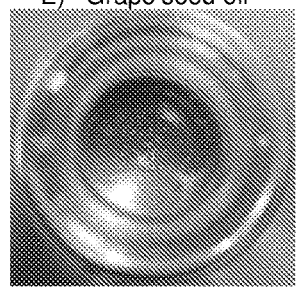
Figure 9:
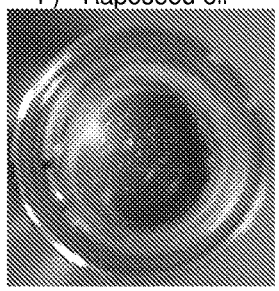
Figure 9:
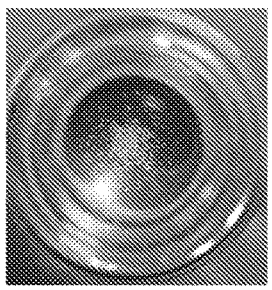
Figure 9:
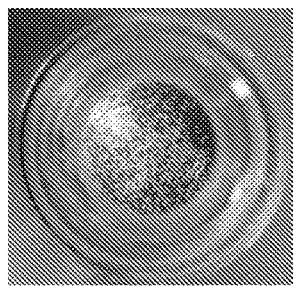
Figure 9:
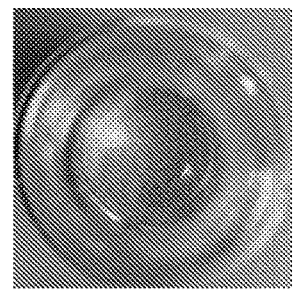
Figure 9:
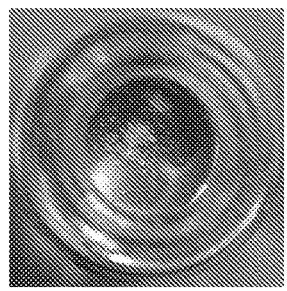

FIG. 9. A-I) Effect of phosphatidylcholine, different oils and tocopherol on dissolution of Cholesterol Crystals, experiment 1. A) Control; B) Phosphatidylcholine; C) Olive oil; D) Ground nut oil; E) Grape seed oil; F) Rapeseed oil; G) Coconut oil; H) Avocado oil; I) hazelnut oil. J-M) Effect of phosphatidylcholine, different oils and tocopherol on dissolution of Cholesterol Crystals, experiment 2. J) Control; K) Almond oil; L) Sunflower oil; M) Tocopherol.

Figure 10:
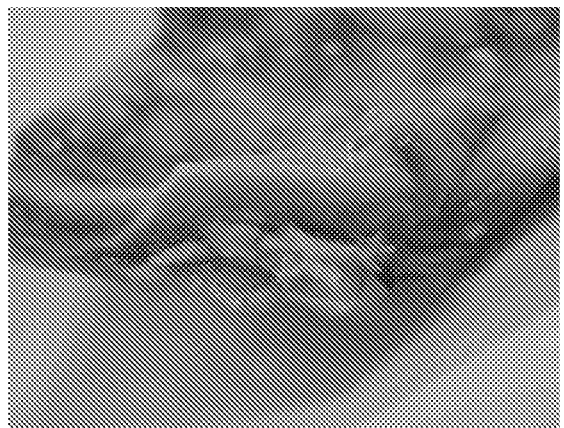
Figure 10:
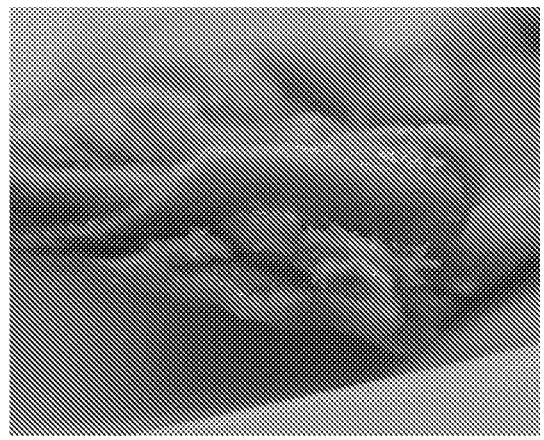
Figure 10:
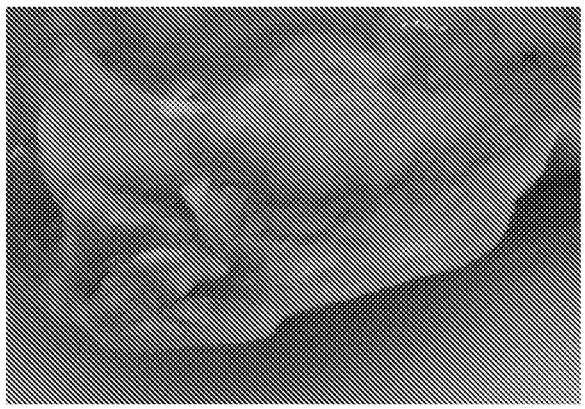
Figure 10:
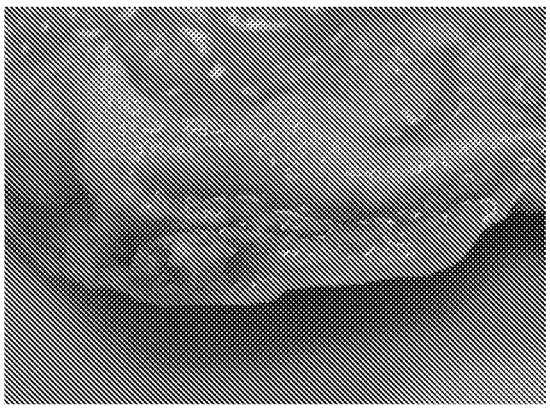
Figure 10:
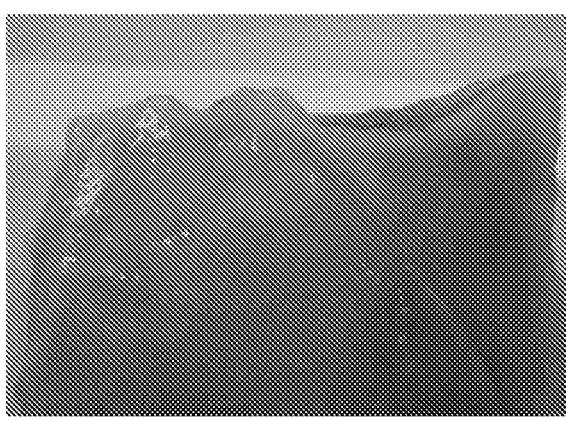
Figure 10:
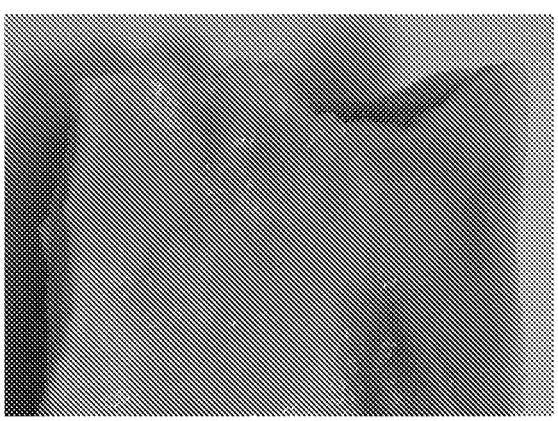

FIG. 10. Abdominal Aorta Cholesterol and Calcium (Phosphate) Crystals. Effect on Cholesterol Crystals. A-B) PBS-ethanol, A) 0 days and B 13 days; C-F) PBS Lycopene in ethanol, C) 0 days, D) 13 days, E) 0 days, F) 13 days.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The invention relates to the treatment of diseases that are associated with the presence of cholesterol crystals in a subject, in particular with the formation and/or presence of cholesterol crystals, and with the process of their disassembly or dissolution. In particular, the present invention provides methods and uses for treating, preventing or attenuating diseases that are associated with cholesterol crystals in a subject. The methods of the present invention comprise administering to the subject a carotenoid compound.

The effect of carotenoid compounds on cholesterol levels in blood serum, that is circulating cholesterol in non-crystalline form, has been described in WO 2013/088156. However, this disclosure is concerned with circulating cholesterol in blood and does not teach the effect of carotenoids on cholesterol crystals, in particular cholesterol crystals that are already formed in a subject.

The inventor has surprisingly found that carotenoid compounds affect the formation, growth, rate of crystallisation of cholesterol, change the physical properties and structure of cholesterol crystals and disrupt/dissemble cholesterol crystals. In particular, formation and/or growth of cholesterol crystals are reduced when the cholesterol crystal is exposed to the carotenoid compound. In an embodiment, the rate of formation and/or rate of growth of cholesterol crystals are reduced when the cholesterol crystal is exposed to the carotenoid compound. The terms "reduced" or "reduction" refer to a reduction compared to a non-treated sample or crystal. Reduction can be at least 10%, at least 20%, at least 30%, at least 40%, at least 50%, at least 60%, at least 70%, at least 80%, at least 90%, or at least 95%

Thus, carotenoid compounds can be used to treat diseases that are characterised by the presence of cholesterol crystals.

Therefore, in one aspect, the invention relates to a carotenoid compound for use in the treatment of a disease associated with the presence of cholesterol crystals wherein the carotenoid compound reduces the formation of cholesterol crystals, such as the rate of formation of cholesterol crystals, reduces growth of cholesterol crystals, such as the rate of growth of cholesterol crystals, changes cholesterol crystal structure, for example disrupts cholesterol crystals and/or changes the size of cholesterol crystals.

In another aspect, the invention provides a method for the prevention and/or treatment of a disease associated with cholesterol crystals in a subject comprising administering to said subject a carotenoid compound wherein said carotenoid compound reduces the formation of cholesterol crystals, such as the rate of formation of cholesterol crystals, reduces growth of cholesterol crystals, such as the rate of growth of cholesterol crystals, changes cholesterol crystal structure, for example disrupts cholesterol crystals and/or changes the size of cholesterol crystals.

In another aspect, the invention provides the use of a carotenoid compound in the manufacture of a medicament for the prevention or treatment a disease associated with cholesterol crystals wherein said carotenoid compound reduces the formation of cholesterol crystals, such as the rate of formation of cholesterol crystals, reduces growth of cholesterol crystals, such as the rate of growth of cholesterol crystals, changes cholesterol crystal structure, for example disrupts cholesterol crystals and/or changes the size of cholesterol crystals.

In another aspect, the invention provides the use of a carotenoid compound in the manufacture of a stent or other graft, medical device, prosthetic or other biocompatible material for the prevention or treatment of a disease associated with cholesterol crystals wherein said carotenoid compound reduces the formation of cholesterol crystals, such as the rate of formation of cholesterol crystals, reduces growth of cholesterol crystals, such as the rate of growth of cholesterol crystals, changes cholesterol crystal structure, for example disrupts cholesterol crystals and/or changes the size of cholesterol crystals. Thus, the presence of carotenoids in these materials prevents formation of cholesterol crystals on their surface(s) to the circulating blood, plasma and/or tissue fluids.

In yet another aspect, the invention provides a stent or other graft, medical device, prosthetic or other biocompatible material coated with a carotenoid compound.

The invention also provides a method for making a stent or other graft, medical device, prosthetic or other biocompatible material comprising the step of coating the stent or other graft, medical device, prosthetic or other biocompatible material with a carotenoid compound.

The invention also provides a method for reducing the formation of cholesterol crystals, such as the rate of formation of cholesterol crystals, reducing growth of cholesterol crystals, such as the rate of growth of cholesterol crystals, changing cholesterol crystal structure, for example disrupting cholesterol crystals and/or changing the size of cholesterol crystals.

In one embodiment, the carotenoid compound inhibits or reduces the formation of cholesterol crystals, for example by affecting the rate of cholesterol crystallisation. In particular, the carotenoid compound inhibits further growth of already formed cholesterol crystals. In one embodiment, the carotenoid compound changes cholesterol crystal structure. In one embodiment of the various aspects and embodiments set out above, the carotenoid compound disrupts or dissembles existing cholesterol crystals, that is cholesterol crystals that are already formed in a subject. Thus, cholesterol crystals are broken up, dissembled or dissolved, and the amount of cholesterol crystals present, for example in a sample or in a subject, is reduced. In particular, in one embodiment, the invention is aimed treating, reducing, dissembling existing cholesterol crystals in a subject. The carotenoid compound is thus administered to specifically target existing cholesterol crystals, that is cholesterol in its crystalline form, and reduces further crystallisation, changes crystal structure and/or dissembles existing cholesterol crystals. In one embodiment, the carotenoid compound is not used to reduce circulating cholesterol that is in non-crystalline form.

The various uses and methods may optionally additionally comprise one of more of the following steps: identifying a subject with cholesterol crystals, assessing whether cholesterol crystals are present in a subject prior to treatment and the step of assessing whether cholesterol crystals are present in a subject after treatment.

Carotenoid compounds are tetraterpenoids which contain long polyene chains. Carotenoid compounds include xanthophylls such as lutein and zeaxanthin, and carotenes, such as beta-carotene, alpha-carotene, zeto-carotene, and lycopene compounds.

In a particular embodiment, the carotenoid is a xanthophyll. In one embodiment, the xanthophyll is selected from the group consisting of α-cryptoxantin, β-cryptoxantin, adonirubin, adonixanthin, alloxanthin, amarouciaxanthin A, antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof.

In one embodiment, the carotenoid is a carotene. In another embodiment, the carotene is selected from the group consisting of α-carotene, β-carotene, γ-carotene, δ-carotene, ε-carotene, ζ-carotene, lycopene, neurosporene, phytoene, phytofluene and combinations thereof.

In one embodiment, the carotenes and xantophylles described above refer to the all-trans forms thereof. In other embodiment, the xantophylles and carotenes for use in the present invention include derivatives containing one or more cis double bond.

In one embodiment, the carotenoid compound is a lycopene compound. Lycopene compounds may include lycopene, 1-HO-3', 4'-didehydrolycopene, 3,1'-(HO) 2-gamma-carotene, 1, 1'-(HO) 2-3, 4, 3', 4'-tetradehydrolycopene, 1, 1'-(HO) 2-3, 4-didehydrolycopene.

In some embodiments, the carotenoid compound is a lycopene compound such as lycopene. Lycopene is an open-chain unsaturated C40 carotenoid of structure I (Chemical Abstracts Service Registry Number 502-65-8, $C_{40}H_{56}$).

Structure I

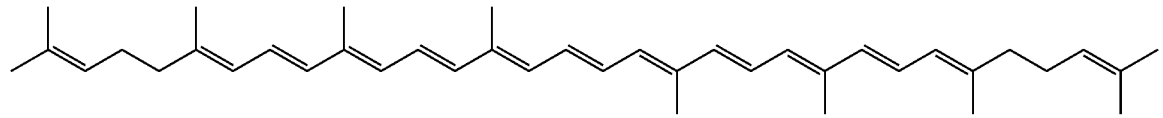 [SMILES: CC(C)=CCC/C(C)=C/C=C/C(C)=C/C=C/C(C)=C/C=C/C=C(C)/C=C/C=C(C)/C=C/C=C(\C)CCC=C(C)C]

Lycopene occurs naturally in plants such as tomatoes, guava rosehip, watermelon and pink grapefruit and any such sources of lycopene may be, for instance, employed.

Lycopene for use as described herein may comprise one or more different isomers. For example, lycopene may include cis-lycopene isomers, trans-lycopene isomers and mixtures of the cis- and trans-isomers. Lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing.

Carotenoid compounds, such as lycopene, for use as describe herein may be natural i.e. obtained from a natural source, for example, extracted from a carotenoid-rich fruit, vegetable or other plant, such as a tomato or melon, or from fungi, algae or bacteria. In one instance, the carotenoid compound may be, or comprise, oleoresin, particularly tomato oleoresin.

A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed.

Carotenoid compounds, such as lycopene, for use as described herein may be synthetic i.e. produced by artificial means, for example, by chemical synthesis. A range of methods for chemical synthesis of lycopene and other carotenoids are known in the art. For example, a three-stage chemical synthesis based on the standard Wittig olefination reaction scheme for carotenoid synthesis may be employed, in which an organic solution of Ci5 phosphonium methanesulfonate in dichloromethane (DCM) and an organic solution of Ci0 dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystalized and dried under heated nitrogen. Synthetic carotenoids, such as lycopene, are also available from commercial suppliers (e.g. BASF Corp, NJ USA).

Synthetic carotenoid compounds, such as lycopene, may comprise an increased proportion of cis isomers relative to natural carotenoid compounds. For example, synthetic lycopene may be up to 25% 5-cis, 1% 9-cis, 1% 13-cis, and 3% other cis isomers, whilst lycopene produced by tomatoes may be 3-5% 5-cis, 0-1% 9-cis, 1% 13-cis, and <1% other cis isomers. Since cis-lycopene has increased bioavailability relative to trans-lycopene, synthetic lycopene is preferred in some embodiments.

Derivatives of carotenoids as described above may be produced by chemical synthesis analogous to the synthesis described above or by chemical modification of natural carotenoids extracted from plant material.

In one embodiment, the cholesterol crystals are in the arterial wall, or in the gallbladder, or in synovial cavities, or in ducts. In one embodiment, the cholesterol crystals are in rich-atheromatous tissues.

In one embodiment, the cholesterol crystals are in aggregates, or crystals or atheromatous tissues are in an artery stent, or other intravascular or vascular devices, or in vascular grafts. Thus, the invention is also aimed at reducing the formation of cholesterol crystals, including existing cholesterol crystals, on medical devices when these are implanted in a subject.

In one embodiment, the disease is atherosclerosis and/or its clinical complications. In one embodiment, this is a cardiovascular disease. In another embodiment, the pathology is a cerebrovascular disease. In another embodiment, the atherosclerosis complication is peripheral arterial disease.

In one embodiment, the disease is gallbladder disease, arthritis associated with cholesterol crystal deposition, or duct narrowing or blockage caused by cholesterol crystallisation.

Atherosclerosis is a syndrome affecting arterial blood vessels. Atherosclerosis results from a chronic inflammatory response in the arterial walls and is a major cause of death and cardiovascular morbidity. Atherosclerosis involves the thickening of artery walls and is characterized by the development of arterial plaque, and the eventual restriction or blockage of blood flow. Current atherosclerosis treatments include diet and lifestyle modifications (e.g. smoking cessation), pharmaceutical intervention (e.g., statins, anti-coagulants, etc.), and surgery (e.g., angioplasty, stents, bypass surgery, etc.).

According to certain embodiments of the present invention, subjects who are treatable by the methods of the invention include, but are not limited to, subjects who have or are diagnosed with atherosclerosis, or who are at risk of developing atherosclerosis. Accordingly, in certain embodiments, the methods of the present invention include selecting a subject having atherosclerosis or at risk of developing atherosclerosis, and administering one or more doses of a carotenoid compound to the subject. As used herein, subjects who are "at risk of developing atherosclerosis" can include subjects who have or exhibit one or more risk factor for atherosclerosis. Risk factors for atherosclerosis are well known in the art and include, without limitation, elevated serum low density lipoprotein (LDL) cholesterol levels, elevated serum triglyceride (TG) levels, reduced serum high density lipoprotein (HDL) cholesterol levels, hypertension, diabetes mellitus, family history, and cigarette smoking. Methods of assessing atherosclerosis risk factors for a given subject are also well known in the art. In one embodiment, the subject has been diagnosed as having cholesterol crystals.

In another embodiment, the disease is cholesterol embolism.

In another embodiment, the disease is an inflammatory disease. An example of such a disease is chronic apical periodontis as cholesterol crystals have been implicated in mediating chronic inflammation.

In another embodiment, the disease is cholecystolithiasis in which precipitation of cholesterol can lead to gallstones and gallbladder inflammation. In another embodiment, the disease is selected from but not limited to Lupus Erythematosus cataract, odontogenic cysts, chronic disease of the middle ear and paranasal sinuses, the kidney, the pituitary and thyroid glands As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

Routes of administration of the carotenoid compound include, for example, oral administration and/or subcutaneous, intravenous, intraperitoneally, intramuscular, or intrasynovial, or epidural, or intradermal injections that provide continuous, sustained levels of the carotenoid compound in the patient.

In one embodiment, delivery can be localised. The carotenoid compound is administered to specifically target existing cholesterol crystals and reduces further crystallisation, changes crystal structure or dissembles cholesterol crystals. Thus, localised delivery to where cholesterol crystals may have formed is one mode of delivery.

In one embodiment, the carotenoid compound is administered as a part of a stent or other graft, medical device, prosthetic or other biocompatible material, which has surfaces or parts exposed to the blood or tissue fluids. The carotenoid compound may thus for part of the coating of a stent or other graft, medical device, prosthetic or other biocompatible material. The resulting stent or other graft, medical device, prosthetic or other biocompatible material has reduced or zero level of cholesterol crystal build up.

The amount of the carotenoid compound that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account. As used herein, the term "effective amount" means an amount of the carotenoid compound, that when administered to a subject, is effective to achieve the desired therapeutic or prophylactic effect under the conditions of administration. For example, the amount of the carotenoid compound to be administered varies with the severity of atherosclerosis. A composition is administered at a dosage that decreases effects or symptoms of atherosclerosis as determined by a method known to one skilled in the art.

Typically, the amount is at least about 0.01% of the carotenoid compound by weight of the composition. When intended for oral administration, this amount can be varied to range from about 0.1% to about 80% by weight of the composition. Preferred oral compositions can comprise from about 4% to about 50% of the active of the present invention by weight of the composition.

Some compositions of the present invention are prepared so that a parenteral dosage unit contains from about 0.01% to about 2% by weight of the carotenoid compound.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

In one embodiment, the carotenoid compound is provided as part of a food stuff. The food stuff can be a functional or medical food or beverage, a dietary supplement, or a nutraceutical product.

In one embodiment, the carotenoid compound is provided as part of a pharmaceutical composition which includes a pharmaceutically acceptable carrier.

In one embodiment, the carotenoid compound is provided as part of a stent or other graft, medical device, prosthetic or other biocompatible material used for implants and which comes into contact with circulating blood. Thus, the invention also relates to a stent or other graft, medical device, prosthetic or other biocompatible material coated with a carotenoid compound. The coating prevents build up of cholesterol crystals on the implant thereby reducing the risk of cardiovascular disease. In one embodiment, the coating may comprise other bioactive compounds. The stent may be a coronary stent. In one embodiment, the stent is a also eluting a carotenoid. In another embodiment, the stent is not eluting a carotenoid.

The pharmaceutical composition can be administered by any convenient route, including but not limited to oral, topical, parenteral, sublingual, rectal, vaginal, ocular, intranasal, pulmonary, intradermal, intrasynovial, epidural, intravitrial, intramuscular, intraperitoneal, intravenous, subcutaneous, intracerebral, transdermal, transmucosal, by inhalation, or topical, particularly to the ears, nose, eyes, or skin or by inhalation.

Parenteral administration includes, for example, intravenous, intramuscular, intraarterial, intraperitoneal, intrasynovial, epidural, intranasal, rectal, intravesical, intradermal, topical or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a carotenoid compound is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. Water is a one carrier. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or pH buffering agents.

The pharmaceutical composition can be in the form of a liquid, e.g., a solution, emulsion or suspension. The liquid can be useful for delivery by injection, infusion (e.g., IV infusion) or sub-cutaneously.

When intended for oral administration, the composition can be in solid or liquid form, e.g. an elixir, syrup, solution, emulsion or suspension, where semi-solid, semi-liquid, suspension and gel forms are included within the forms considered herein as either solid or liquid. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e.g. a gelatin capsule), it can contain, in addition to materials of the above type, a liquid carrier such as polyethylene glycol, cyclodextrin or a fatty oil.

Pharmaceutical compositions may be formulated to release the carotenoid compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target atherosclerosis using carriers or chemical derivatives to deliver the therapeutic agent to a particular cell type (e.g., endothelial cells or smooth muscle cells). For some applications, controlled release formulations obviate the need for frequent dosing during the day to sustain the plasma level at a therapeutic level. Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the carotenoid compound is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Compositions can take the form of one or more dosage units.

In one embodiment, administration of the carotenoid compound is part of a combination therapy. The carotenoid compound may be co-administered with the other therapy or given at another time. In another embodiment, the subject may have previously received another therapy, such as a statin based therapy.

Also provided herein is a method for changing or disrupting cholesterol crystal structure comprising exposing a cholesterol crystal to a carotenoid compound. In one embodiment, the optical and/or electron transfer properties of cholesterol crystal are changed. Also provided herein is an in vitro or in vivo method for reducing the formation, rate of formation, growth or rate of growth of cholesterol crystals, comprising exposing a cholesterol crystal to a carotenoid compound. In these methods, the ratio of concentration of the carotenoid compound to cholesterol can be, for example, 1:10 to 1:10$^6$.

Another aspect relates to a cholesterol crystal obtained or obtainable by the method of described above. As can be seen in the examples, the exposure to cholesterol results in a needle shaped crystal.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1

Prevention of or Interference into the Formation of Cholesterol Crystals.

A solution of 198 ml of 1 g of cholesterol (Sigma) in 99% ethanol was divided in two equal parts. In one part 1 ml of ethanol containing 100 μg of the dissolved lycopene was added. This provided ratio of lycopene to cholesterol as 1:10$^6$. Into the other part, the control, 1 ml of the ethanol itself was added. Then both samples were left in the dark room for evaporation under 20-22° C. Recording of the status of the both samples were made at least on a daily or even shorter intervals. Some results of this experiment are presented in FIG. 1 A-N

It was observed that presence of lycopene at a concentration of less than one molecule per million molecules of cholesterol can significantly affect the rate of its crystallisation. Firstly, floating cholesterol crystals were already observed in the control sample after two days of the evaporation. No signs of these crystals were observed in the presence of lycopene even on the 4$^{th}$ day, and they only started to appear there on the 6$^{th}$ day of the experiment. At the same time, a solid crust of crystallised cholesterol was already covering all surface of the control solution. On the 12$^{th}$ day, there was no solvent left in the control and cholesterol turned to the solid crystallised mass, while in the sample where lycopene was present, the process of crystallisation was still on-going. By 14$^{th}$ day, this was completed.

Example 2

Changes of Physical Properties of Cholesterol Crystals.

In a range of experiments where ratio of cholesterol to lycopene varied, from 1,000 to at least 10,000,000 molecules of the former to 1 molecule of the latter, noticeable changes in the physical properties of crystals were observed.

In all control experiments, cholesterol crystallised into a plate-like crystals, see FIG. 2B and FIG. 2D. Sometimes they could create a thick flat plate of few centimetres across, like the one on the bottom of the glass in the experiment 2, FIG. 2C. However, when lycopene was present in the medium a formation of a new type of crystals was observed. There were significantly smaller and in a shape of needle- or narrow tube-like crystals:

FIG. 2B, 2C and

FIGS. 3B, 3D and 4B.

Under the light and confocal microscopy these difference between two types of cholesterol crystals, in size and shape, are more evident (FIGS. 5A-F and 6A-B).

It was interesting to observe that the slowing down of the crystallisation process caused by lycopene resulted by slowing rate of ethanol evaporation. This could be explained that this carotenoid by disrupting cholesterol folding into the crystal structure, reduces the entropy, which is released during this process, and essentially cooling down the solvent and its evaporation. As a result of this the amount of ethanol in the lycopene containing sample was almost twice as much as in the control sample—experiment 1 in FIG. 2.

Moreover, lycopene not only changed the physical properties of cholesterol crystals per se, but it was also able to incorporate into newly formed crystal structures. This creates new types of chromophore crystals which would be expected to have different optical and electron transfer properties.

In summary, these observations indicate that lycopene can significantly affect cholesterol crystal folding, change its existing physical properties of cholesterol crystals and create new properties of cholesterol crystals.

Example 3

Use of Carotenoids to Disassemble Cholesterol Crystals—Lycopene.

To 100 mg of crystallised cholesterol (Sigma) 20 ml of ethanol solutions with different concentrations of lycopene were added. As a control, 20 ml of the same ethanol was used but without any lycopene. After gentle stirring for a couple of minutes, under the room temperature of about 20-22° C., recording of the results was made.

This experiment was repeated a number of times at different range of lycopene concentrations. Under these conditions, lycopene was able to reduce the number and size of cholesterol crystals at a ratio of about 1 molecule of lycopene per 1,000,000 of molecules of cholesterol or higher. When the ratio reached 1 to 100,000, a complete disaggregation of these crystals was observed (FIG. 7A-F).

Example 4

Use of Carotenoids to Disassemble Cholesterol Crystals—Lutein.

To 100 mg of crystallised cholesterol (Sigma) 20 ml of ethanol solutions with different concentrations of lutein were added. As a control, 20 ml of the same ethanol was used but without any lutein. After gentle stirring for a couple of minutes, at a room temperature of about 20-22° C., recording of the results was made.

This experiment was repeated a number of times at different range of lutein concentrations. Under these conditions, lutein was able to reduce the number and size of cholesterol crystals at a ratio of about 1 molecule of lutein per 100,000 of molecules of cholesterol, or higher. When the ratio reached 1 to 20,000 a complete disaggregation of these crystals occurred (FIG. 7A-F).

Example 5

Evidence that Some Oils, Phospholipids, Hydrophobic Vitamins do not Facilitate Disassemble of Cholesterol Crystals.

This experiment had two objectives. On the one hand, it was important to check whether the ability of lycopene or lutein in the described above experiments, was due to these carotenoids or perhaps to oils, which are typically present in their commercial preparations. On the other hand, it was important to assess how widespread the observed disruptive cholesterol folding properties of carotenoids were.

To 100 mg of crystallised cholesterol (Sigma) 20 ml of ethanol solutions with different concentrations of a number of biologically active hydrophobic substances and oils were added. As a control, 20 ml of the same ethanol was used but without any additives. After gentle stirring for a couple of minutes, at a room temperature of about 20-220°, recording of the results was made.

The results presented in FIG. 9 A-M demonstrate that neither olive nor sunflower oils, which are typically used to make commercial preparations of carotenoids in general, and lycopene and lutein in particular, affected the size or number of the cholesterol crystals in the test system. Also, no effects on cholesterol crystals was seen when grape seed, rapeseed, hazelnut, avocado, coconut, groundnut nor almond oils were tested. A strong emulsifier and one of the main phospholipida in biological systems, phosphatidylcholine, was also not able to affect cholesterol crystals. Furthermore, one of the most abundant hydrophobic vitamins, tocopherol, was also ineffective.

Example 6

Use of Carotenoids to Disassemble Cholesterol Crystals in the Arterial Wall.

It was important to confirm whether carotenoids, and lycopene in particular, can affect folding of cholesterol crystals, which are not just synthesized by a manufacturer, but produced naturally, and particularly those, which are developed during pathological process in human. For this purpose, we used pieces of atherosclerotic abdominal aorta, which were obtained during a combined vascular graft and by-pass surgery.

Comparable types of atherosclerotic lesions were collected. This was in terms of their stage of development, with prominently featured cholesterol crystals of similar size, embedded into the atheromatous tissues of the aorta wall. As a control material we collected pieces of the atherosclerotic abdominal aorta containing calcium phosphate crystals.

Firstly, an ethanol solution 1 µg/ml of lycopene was prepared. It was then diluted by PBS 10 fold. As a control, a solution was made with the same ratio ethanol to PBS but without lycopene. Then pieces of aorta were incubated, in light protected containers at the room temperature of about 20-220° for 13 days. The results of this experiment are presented in FIG. 10 (A-F).

Incubation in PRS-ethanol solution did not affect size, composition or architecture of the lesion. At the same time, incubation of a similar lesion with lycopene solution resulted in noticeable changes. These included:
  instead of three crystalloid structures, by the end of the incubation period there were only two,
  the size of these remaining structures was reduced by at least two-fold,
  the size of the surrounding cholesterol-rich atheromatous mass of the lesion was also reduced by about two-fold.

It was interesting that in the control experiment lycopene-ethanol-PBS solvent did not affect size or shape of calcium phosphate crystals formed in the atherosclerotic plaque. This indicates that lycopene can disrupt folding of already formed cholesterol crystals, but not mineral ones.

To conclude, this experiment suggests that carotenoids, and lycopene in particular, can be used not only for the prevention of the formation of new cholesterol crystals, but also to help to disaggregate already formed ones in biological, in particular human tissues.

REFERENCES

1. Lawrence Rajendran, Hans-Joachim Knolker & Kai Simons—*Subcellular targeting strategies for drug design and delivery. Nature Reviews Drug Discovery* (2010) 9, 29-42.
2. David J Hawkes and Johnson Mak—*Lipid Membrane; A Novel Target for Viral and Bacterial Pathogens. Current Drug Targts* (2017) v. 18, 16, 1615-1621.
3. Dowing R H—Review: pathogenesis of gallstones. *Aliment Pharmacol Ther.* 2000 May; 14 Suppl 2:39-47.
4. Steven M Strasberg—*The Pathogenesis of Cholesterol Gallstones—A Review. Journal of Gastrointestinal Surgery react-text:* 55 2(2):109-25.
5. Laura M. Stinton and Eldon A. Shaffer—*Epidemiology of Gallbladder Disease: Cholelithiasis and Cancer. Gut and Liver, Vol.* 6, No. 2, April 2012, pp. 172-187.
6. George S. Abela, and Kusai Aziz—*Cholesterol Crystals Rupture Biological Membranes and Human Plaques during Acute Cardiovascular Events—A Novel Insight into Plaque Rupture by Scanning Electron Microscopy. Scanning* (2006) v. 28, 1-10.
7. George S. Abela, Kusai Aziz, Ameeth Vedre, Dorothy R. Pathak, John D. Talbott, and Joyce DeJong.—*Effect of Cholesterol Crystals on Plaques and Intima in Arteries of Patients With Acute Coronary and Cerebrovascular Syndromes. The American Journal of Cardiology* (2009), 103, 959-968.
8. George S. Abela—*Cholesterol crystals piercing the arterial plaque and intima trigger local and systemic inflammation. Journal of Clinical Lipidology* (2010) 4, 156-164.
9. Richard J Frank—*Parallel cholesterol crystals: A sign of impending plaque rupture. J Clin Exp Cardiolog* (2013), v4:4, p 74.
10. Richard Conti—*Hypothermia: Is it Good for the Brain and Not for the Arteries? JACC* (2013), Vol. 61, No. 20, 2110-4.
11. Yamaji K, Inoue K, Nakahashi T, Noguchi M, Domei T, Hyodo M, Soga Y, Shirai S, Ando K, Kondo K, Sakai K, Iwabuchi M, Yokoi H, Nosaka H, Nobuyoshi M, Kimura T.—*Bare metal stent thrombosis and in-stent neoatherosclerosis. Circ Cardiovasc Interv.* 2012 Feb. 1; 5(1):47-54.

12. Kang S J, Ahn J M, Han S, Park D W, Lee S W, Kim Y H, Lee C W, Park S W, Mintz G S, Park S J.—*Multimodality imaging of attenuated plaque using grayscale and virtual histology intravascular ultrasound and optical coherent tomography.* Catheter Cardiovasc Interv. 2016 July; 88(1):E1-E11.
13. Takigawa T1, Matsumaru Y, Kubo T, Fukuhara N, Hayakawa M, Usui M.—*Recurrent subacute in-stent restenosis after carotid artery stenting due to plaque protrusion.* Neurol Med Chir (*Tokyo*). 2009 September; 49(9): 413-7.
14. M A Rodriguez, H Paul, I Abadi, et al.—*Multiple microcrystal deposition disease in a patient with systemic lupus erythematosus.* Ann Rheum Dis 1984 43: 498-502.
15. I W J Hurley, A M V Brooks, D P Reinehr, G B Grant, W E Gillies—*Identifying anterior segment crystals. British Journal of Ophthalmology,* 1991, 75, 329-331
16. Firoz Iqbal—*The relationship between cholesterol crystals, foamy macrophages and haemosiderin in odontogenic cysts.* Masters of Dental Science (2008) The University of Sydney, New South Wales, Australia.
17. Cinthya Bessa da Motta Almada, Debora Rodrigues Fonesca, Rachel Rego Vanziflotta, Fábio Ramôa Pires—*Cholesterol Granuloma of the Maxillary Sinus. Braz Dent J* (2008) 19(2): 171-174.
18. Gowreeson Thevendran1, Mahmoud Al-Akraa1, Stephen Powis1 and Neil Davies—*Cholesterol granuloma of the kidney mimicking a tumour. Nephrol Dial Transplant* (2003) 18: 2449-2450.
19. F. Parkes Weber, C. Worster-Drought and W. E. Carnegie Dickson—*Cholesterol Tumour (Craniopharyngioma) of the Pituitary Body. J Neurol Psychopathol* 1934 s1-15, 39-45.
20. Maurice N. Richter, and Kenneth S. McCarty—Anisotropic Crystals in the Human Thyroid Gland. Am J Pathol. 1954 June; 30(3): 545-553.
21. Channabasaveshwar V. Y., Govindaswamy Sh., Uma S. H. and Subbarao K. P.—*Cholesterol-based nonsymmetric liquid crystal dimers: an overview. J. Mater. Chem.* (2008) 18, 2927-2949.
22. Ray Abhijit—*Liquid Crystal—A Review. Asian Journal of Research In Chemistry* (2012) v.5, 4, 563-567.
23. Jong Hwa Jung, Seok-Hoon Lee, Jong Shin Yoo, Kaname Yoshida, Toshimi Shimizu, Seiji Shikai—*Creation of Double Silica Nanotubes by Using Crown-Appended Cholesterol Nanotubes. Chemistry a European Journal* (2003) v.9, 21, p. 5307-5313.
24. Pengyao Xing, Hongzhong Chen, Linyi Bai and Yanli Zhao—*Photo-triggered transformation from vesicles to branched nanotubes fabricated by a cholesterol-appended cyanostilbene. Chem. Commun.* (2015) 51, 9309-9312.
25. Abela (2010) *Role of cholesterol crystals in myocardial infarction and stroke, Clinical Lipidology,* 5:1, 57-69
26. Ridker The JUPITER Trial Results, *Controversies, and Implications for Prevention Circ Cardiovasc Qual Outcomes.* 2009; 2:279-285
27. Nidorf et al *Targeting Cholesterol Crystal-Induced Inflammation for the Secondary Prevention of Cardiovascular Disease Journal of Cardiovascular Pharmacology and Therapeutics* 00(0), 1-8, 2013
28. Johnson et al *Traditional Clinical Risk Assessment Tools Do Not Accurately Predict Coronary Atherosclerotic Plaque Burden: A CT Angiography Study, AJR:*192, January 2009 235-243
29. Petersen *Plasma lipid oxidation predicts atherosclerotic status better than cholesterol in diabetic apolipoprotein E deficient mice. Experimental Biology and Medicine* 2017; 242: 88-91

The invention claimed is:

1. A method for inducing disassembly of cholesterol crystals in a subject in need thereof, the method comprising orally administering to said subject a composition comprising a carotenoid compound at a concentration sufficient to induce disassembly of the cholesterol crystals.

2. The method according to claim 1, wherein the carotenoid compound is selected from a lycopene, lutein, zeaxanthin, meso-zeaxanthin, astaxanthin, carotenes, cryptoxanthins, flavoxanthin, neoxanthin and a tetraterpenoid.

3. The method according to claim 2, wherein the carotenoid compound is a lycopene.

4. The method according to claim 1, wherein the subject has a disease associated with cholesterol crystals is selected from cardiovascular disease, cerebrovascular disease, peripheral artery disease, aortic aneurysm, arterial aneurysm, gallstone disease, renal artery stenosis, mesenteric ischemia, intestinal ischemia, chronic disease of the middle ear paranasal sinuses, and chronic kidney disease.

5. The method according to claim 1, wherein the composition is a nutraceutical composition.

6. The method according to claim 1, wherein the composition comprises 4% to about 50% of the carotenoid compound.

7. The method according to claim 1, wherein the composition is formulated into a powder, a granule, a compressed tablet, a pill, a capsule, or a chewing gum.

* * * * *